| United States Patent [19] | [11] Patent Number: 4,733,007 |
| Andrade et al. | [45] Date of Patent: Mar. 22, 1988 |

[54] PROCESS FOR THE PRODUCTION OF 1,12-DODECANOIC DIACID

[75] Inventors: Juan Andrade, Ridgewood, N.J.; Klaus Koehler, Hainburg; Guenter Prescher, Hanau, both of Fed. Rep. of Germany

[73] Assignee: Degussa Aktiengesellschaft, Frankfurt am Main, Fed. Rep. of Germany

[21] Appl. No.: 77,843

[22] Filed: Jul. 27, 1987

[30] Foreign Application Priority Data

Aug. 23, 1986 [DE] Fed. Rep. of Germany ....... 3628664

[51] Int. Cl.$^4$ ........................................... C07C 51/235
[52] U.S. Cl. ...................... 562/534; 502/152; 502/155; 502/166; 502/213; 502/222; 502/229; 560/190; 562/522; 562/590
[58] Field of Search ..................... 562/522, 534, 590; 560/190; 502/152, 155, 166, 213, 222, 229

[56] References Cited

U.S. PATENT DOCUMENTS

| 4,148,822 | 4/1979 | Ogawa et al. | 562/534 |
| 4,404,397 | 9/1983 | Daniel | 562/534 X |
| 4,410,725 | 10/1983 | Decker et al. | 562/534 |
| 4,613,694 | 9/1986 | Rossi et al. | 562/590 |
| 4,634,795 | 1/1987 | Bar-Tana | 562/590 |

*Primary Examiner*—Werren B. Lone
*Assistant Examiner*—Vera C. Clarke
*Attorney, Agent, or Firm*—Beveridge, DeGrandi & Weilacher

[57] ABSTRACT

A process for the production of 1,12-dodecanoic diacid by hydroformylating an unsaturated carboxy compound in the presence of a rhodium catalyst and oxidation of the aldehyde with oxygen, wherein undecyl-10-ene-acid is hydroformylated in the presence of hydridotristriphenylphosphine-rhodium-carbonyl combined with triphenylphosphine and/or triphenylphosphite, and the 11-formyl undecanioc acid which is thus formed is oxidized with oxygen in the presence of inorganic and organic Co(II) salts.

12 Claims, No Drawings

PROCESS FOR THE PRODUCTION OF 1,12-DODECANOIC DIACID

The present invention relates to a process for the production of 1,12-dodecanoic diacid.

It is known to produce this acid by oxidation and saponification of methyl-11-aldehyde-undecanoate beginning with the hydroformylating of methyl undecylenate (H. Adkins, G. Krsek, JACS, Vol. 70, January 1948, p. 383–386).

Also known are hydroformylated products obtained only on a double bond, where 1,9-decadiene is reacted with carbon monoxide and hydrogen in the presence of a rhodium compound as a catalyst.

Undecene aldehydes are obtained according to DE-OS No. 27 24 484 and following oxidation and saponification thereof can be used as starting compounds according to the Adkins and Krsek process.

It is accordingly an object of the invention to provide a novel process for the production of 1,12-dodecanoic diacid.

It is a feature of the present invention to provide a process for the production of 1,12-dodecanoic diacid by hydroformylating an unsaturated carboxy compound in the presence of a rhodium catalyst to produce an aldehyde, followed by oxidation of the aldehyde thus formed with oxygen. It is a further feature of the invention to carry out a process wherein undecyl-10-ene acid is hydroformylated in the presence of a complex catalyst that is hydridotris-triphenylphosphine-rhodium-carbonyl combined with triphenylphosphine and/or triphenylphosphite and the 11-formyl undecanoic acid which is thus formed is oxidized with oxygen in the presence of inorganic or organic Co-(II) salts.

The 11-formyl undecanoic acid is hydroformylated with a gaseous mixture of hydrogen and carbon monoxide in the presence of a catalyst. The reaction generally occurs at temperatures of from 80° to 140° C., preferably at temperatures of from 80° to 120° C. The pressure can be selected as desired from within a wide range, but it is preferable to work in the pressure range of from 1 to 12 bar. Pressures of from 2 to 8 bar are preferred. Hydroformylation reactions of this type are widely understood in the art.

It is recommended to use the smallest required stoichiometric quantities, preferably 1.05 to 2.5 times the quantities, of hydrogen and carbon monoxide, for the reaction, in which the mole ratio of hydrogen to carbon monoxide can be selected as desired from within a wide range, but preferably is between 0.5 to 1.0 to 1.0 to 0.5.

Hydridotris-triphenylphosphine-rhodium-carbonyl combined with triphenylphosphine and/or triphenylphosphite serves as catalyst in hydroformylating. Such catalysts are described in DE-AS No. 17 93 069 which is relied on and incorporated herein by reference. For execution of the process according to the invention, preferably 0.002 to 0.01 parts by weight of the hydridotris-triphenylphosphine-rhodium-carbonyl and a total of 0.02 to 0.3 parts by weight of the triphenylphosphine and/or triphenylphosphite are used per part by weight of undecyl-10-ene-acid. The amounts of the individual phosphine and phosphite can be widely varied.

The 11-formyl undecanoic acid obtained from the hydroformylation is separated from the reaction mixture in one preferred modification of the process according to the invention and then is oxidized at 10° to 100° C., preferably 40° to 90° C., in the presence of an organic or inorganic Co(II) salt with a gas containing oxygen or with pure oxygen until the reaction is completed.

It is preferred to use 0.005 to 0.09 parts by weight of the Co(II) salt, preferably 0.01 parts by weight, especially of Co(II) acetate, per part by weight of 11-formyl undecanoic acid.

In one particular embodiment of the invention, the oxidation is carried out in the presence of a percarboxylic acid in a quantity of 0.002 to 0.2 parts by weight based on the compound to be oxidized. Peracetic and perpropionic acids are preferred in this respect.

The resulting 1,12-dodecanoic diacid obtained in the process is separated from the oxidation mixture by known measures following termination of the reaction and cooling.

In accordance with one aspect of the invention, the oxidation process is carried out directly in the solution formed during the hydroformylating reaction, with separation, and the aforementioned reaction parameters are still retained.

In one preferred embodiment of the invention, an inert organic solvent, preferably an aromatic such as for instance benzene or toluene is present in the mixture used for the hydroformylating or oxidation.

The present invention will be described in further detail in the following illustrative examples.

EXAMPLE 1

Undecyl-10-ene-acid (64.5 g) in 150 ml of toluene was placed in an agitated autoclave with 8.4 g of triphenylphosphine and 0.44 g of hydridotris-triphenylphosphine-rhodium-carbonyl complex. Then a mixture of equal volume parts hydrogen and carbon monoxide was fed into the autoclave reactor under 6 bar pressure. The temperature in the autoclave was held at 115° C. After 300 min., no additional gas was absorbed and the feed was terminated. The NMR (nuclear magnetic resonance) analysis showed that 85% of the undecyl-10-ene-acid had been reacted. The reaction mixture which contained the 11-formyl undecanoic acid was recrystallized following drainage of the acetone solvent. The 11-formyl undecanoic acid yield was 28.2 g=37.3%.

EXAMPLE 2

10 g of 11-formyl undecanoic acid, as synthesized in Example 1, dissolved in 50 ml toluene, were treated at 60° C. with 30 mg Co(II) acetate and 1 ml 25% perpropionic acid and then gaseous oxygen was applied to the mixture for over a period of 5 hours. With cooling, 1,12-dodecanoic diacid was deposited. 9.7 g (90%) were isolated.

EXAMPLE 3

Example 1 was reproduced, but the reaction mixture was treated with 0.7 g of Co-(II) acetate and 100 ml toluene following termination of the gas absorption, and then heated to 60° C. and contacted with 2 ml 25% perpropionic acid. Then gaseous oxygen was applied for 5 hours and 1,12-dodecanoic diacid was crystallized out upon cooling. The yield was 70% based on the undecyl-10-ene-acid which was used.

Further variations and modifications of the present invention will be apparent to those skilled in the art from the foregoing and are intended to be encompassed by the claims appended hereto.

The entire disclosure of German priority application No. P 36 28 664.8 is relied on and incorporated by reference.

We claim:

1. A process for the production of 1,12-dodecanoic diacid comprising selecting undecyl-10-ene-acid as an unsaturated carboxy compound and hydroformylating said compound in the presence of a rhodium complex catalyst to form the corresponding aldehyde in a reaction mixture, said catalyst being hydridotris-triphenylphosphine-rhodium-carbonyl combined with triphenylphosphine and/or triphenylphosphite, and thereafter oxidizing the 11-formyl undecanoic acid which is thus formed with oxygen in the presence of an inorganic or organic Co(II) salt.

2. The process as set forth in claim 1, further comprising separating 11-formyl undecanoic acid from the reaction mixture and then subjecting said acid to oxidation.

3. The process as set forth in claim 1, wherein the 11-formyl undecanoic acid is oxidized in the reaction mixture.

4. The process as set forth in claim 1, wherein 0.002 to 0.01 parts by weight of the hydridotris-triphenylphosphine-rhodium-carbonyl and 0.02 to 0.3 parts by weight of the triphenylphosphine and/or triphenylphosphite are used per part by weight of the undecyl-10-ene acid.

5. The process as set forth in claim 1, wherein the hydroformylating is carried out at temperatures of from 80° to 140° C. and pressure of from 1 to 12 bar.

6. The process as set forth in claim 1, wherein the oxidation is carried out at a temperature of from 10° to 100° C.

7. The process as set forth in claim 6, wherein the temperature is from 40° to 90° C.

8. The process as set forth in claim 1, wherein from 0.005 to 0.09 parts by weight of the Co(II) salt is used per part by weight of the 11-formyl undecanoic acid.

9. The process as set forth in claim 1, wherein Co(II)-acetate is the organic salt.

10. The process as set forth in claim 1, wherein the hydroformylation is conducted with hydrogen and carbon monoxide and hydrogen.

11. The process as set forth in claim 1, further comprising adding a percarboxylic acid to the oxidizing reaction.

12. The process as set forth in claim 11, wherein 0.002 to 0.2 parts by weight of the percarboxylic acid is used for each part by weight of the 11-formyl undecanoic acid.

* * * * *